(12) United States Patent
Kellner et al.

(10) Patent No.: US 7,348,160 B2
(45) Date of Patent: Mar. 25, 2008

(54) PHOSPHOAMIDASE ASSAY

(75) Inventors: Roland Kellner, Heppenheim (DE); Ansgar Wegener, Heusenstamm (DE)

(73) Assignee: Merck Patent GmbH, Darmstadt (DE)

( * ) Notice: Subject to any disclaimer, the term of this patent is extended or adjusted under 35 U.S.C. 154(b) by 251 days.

(21) Appl. No.: 10/501,077

(22) PCT Filed: Oct. 10, 2003

(86) PCT No.: PCT/EP03/11253

§ 371 (c)(1),
(2), (4) Date: Jul. 9, 2004

(87) PCT Pub. No.: WO2004/044233

PCT Pub. Date: May 27, 2004

(65) Prior Publication Data

US 2005/0124023 A1    Jun. 9, 2005

(30) Foreign Application Priority Data

Nov. 9, 2002    (EP) ................... 02025128

(51) Int. Cl.
*C12Q 1/34*    (2006.01)
*G01N 33/53*    (2006.01)
(52) U.S. Cl. ....................... 435/18; 435/7.72
(58) Field of Classification Search ............ None
See application file for complete search history.

(56) References Cited

U.S. PATENT DOCUMENTS 6,812,015 B1 * 11/2004 Klumpp et al. ............. 435/195

OTHER PUBLICATIONS

Mountfort et al. Evaluation of the Fluorometric Protein Phosphatase Inhibition Assay in the Determination of Okadaic Acid in Mussels; Toxicon, vol. 37 (1999) pp. 909-922.*
Kim et al. Protein Phosphatases 1, 2A, and 2C are Protein Histidine Phosphatases; The Journal of Biological Chemistry, vol. 268, No. 25 (1993) pp. 18513-18518.*
IUBMB Enzyme Nomenclature, EC 3.9.1.1 (1961)□□http://www.chem.qmul.ac.uk/iubmb/enzyme/EC3/9/1/1.html.*
Hiraishi et al. Bovine Liver Phosphoamidase as a Protein Histidine /Lysine Phosphatase; J. Biochem, vol. 126 (1999) pp. 368-374.*
Ek et al. Identification and Characterization of a Mammalian 14-kDa Phosphohistidine Phosphatase; European Journal of Biochemistry, vol. 269 (2002) pp. 5016-5023.*

* cited by examiner

*Primary Examiner*—Jon Weber
*Assistant Examiner*—Paul Martin
(74) *Attorney, Agent, or Firm*—Millen, White, Zelano, Branigan, P.C.

(57) ABSTRACT

The present invention relates to the use of compounds and to methods for the qualitative and/or quantitative determination of the activity of phosphoamidases or protein phosphoamidases specific for hydrolyzing phosphoamide (P—N) bonds N-phosphorylated basic amino acids like phospholysine, phosphoarginine and phosphohistidine.

7 Claims, 11 Drawing Sheets

PHOSPHOAMIDASE ASSAY

This application claims the benefit of priority as a 317 of PCT/EP03/11253 filed Oct. 10, 2003 and EPO (European Patent Office) 02025128.6 filed Nov. 9, 2002.

FIELD OF THE INVENTION

The present invention relates to the use of compounds and to methods for the detection, characterization and qualitative and/or quantitative determination of the activity of phosphoamidases or protein phosphoamidases specific for hydrolyzing phosphoamide (P—N) bonds of N-phosphorylated basic amino acids like phospholysine, phosphoarginine and phosphohistidine or of peptides comprising these phosphorylated amino acids.

BACKGROUND OF THE INVENTION

Communication between individual cells in multicellular organisms is essential for the regulation and coordination of complex cellular processes such as growth, differentiation, migration and apoptosis. Signal transduction networks mediating these biological mechanisms use reversible protein phosphorylation as a fundamental tool. According to a modest estimation about one third of the known proteins can be phosphorylated in eukaryots. In the past decades it turned out that a multitude of regulatory cycles are intimately interlocked through overlapping substrates and the mutual regulation of kinases and phosphatases via phosphorylation/dephosphorylation by other kinases and phosphatases, respectively (Cohen, P. (2000) Trends Biochem. Sci. 25, 596-601). Deregulation of enzymatic dephosphorylation will cause substantial malfunctions and therefore are causal for diseases.

Protein phosphatases are grouped according to their activity on the various phospho-amino acids, namely the most prominent phosphorylated amino acids serine (Ser), threonine (Thr) and tyrosine (Tyr). However, further amino acids need to be considered as relevant phospho-derivatives, namely histidine (His), lysine (Lys) cysteine (Cys), aspartic acid (Asp), and glutamic acid (Glu). Systematic classification of kinases concern the nature of the phosphate accepting amino acids, e.g. whether a phosphate ester, thio ester, phospho-amidate or phosphate carboxylate anhydride is formed (Matthews, H. R. & Chan, K. (2001) Methods Mol. Biol. 124: 171-182).

The phospho-amino acids His, Asp, Glu, Lys and Cys show distinct chemical properties like acid-lability and faster physiological turnover which are commonly used for characterization (Sickmann, A. & Meyer, H. E. (2001) Proteomics 1, 200-206). Up to now the less abundant phospho-amino acids predominantly showed up in cellular processes of bacteria, plants (Chang, C. & Meyerowitz, E. M. (1995) Proc. Natl. Acad. Sci. USA 92, 4129-4133) and lower eucaryots (Huang, J. M. et al. (1991) J. Biol. Chem. 266, 9023-9031). Due to their high-energy phosphate bonds they are utilized in rapid phosphotransfer reactions like the two-component system and the phospho-relay signaling (West, A. H. & Stock, A. M. (2001) Trends Biochem. Sci. 26, 369-376).

Most recently, histidine phosphorylation was identified to contribute to regulatory processes in vertebrates like stimulation of human platelets (Crovello, C. S. et al. (1995) Cell 82, 279-286) or regulating annexin I-function (Muimo, R. et al. (2000) J. Biol. Chem. 275, 36632-36636). Another well established example is the regulative phosphorylation of ATP-citrate lyase by nucleoside diphosphate kinase. (NDPK) (Wagner, P. D. & Vu, N. D. (1995) J. Biol. Chem. 270, 21758-21764). However, protein phosphoamidases acting specific on phospho-amidates in proteins like histidine phosphorylated proteins are rarely described. First evidence for such like phosphoamidase activity was found as additional function of PP1 and PP2A when acting on P-His histone 4 (Kim, Y. et al. (1993) J. Biol. Chem. 268, 18513-18518; Kim, Y. et al. (1995) Biochim. Biophys. Acta 1268, 221-228). Although histidine phosphate is known to be present in mammals (Crovello, C. S. et al. (1995) Cell, 82:279-286), it has not to date been possible to identify either the corresponding kinases or the relevant phosphoamidases. A protein with assigned specific phosphoamidase activity, recognizing amongst other substrates P-His-NDPK but not hydrolyzing O-phosphorylated substrates, was isolated from bovine liver but no sequence identity is published (Hiraishi, H. et al. (1999) J. Biochem. (Tokyo) 126, 368-374). Furthermore, a 17-kDa phosphoamidase that is specific only for phosphorylated Arg and is free of the activity that hydrolyzes O-phosphorylated compounds has been described (Kuba, M. et al. (1992) Eur. J. Biochem. 208, 747-752; Yokoyama, K., et al. (1993) J. Biochem. 113, 236-240 Kumon, A. et al. (1996) J. Biochem. 119, 719-724).

A protein phosphoamidase specific for hydrolyzing N-phosphorylated histidine residues in peptides or proteins and having no activity that hydrolyzes O-phosphorylated peptides or proteins is PHP1 (WO 00/52175; Ek, P. et al. (2002) Eur. J. Biochem. 269, 5016-5023).

In scope to understand the physiological role of phosphoamidases and to be able to interact with patho-physiological situations it is important to identify the enzyme-substrate specificity of a phosphoamidase unequivocally, and to develop tools to interfere by means of an inhibition or activation of the enzyme.

Within the meaning of the present invention the term "phosphoamidase" defines an enzyme hydrolyzing phosphoamide (P—N) bonds of phosphorylated basic amino acids like P-His, P-Lys, P-Arg, or of peptides or proteins comprising these phosphorylated amino acids and which is devoid of an activity that hydrolyzes O-phosphorylated proteins or peptides. Examples for such phosphoamidases within the meaning of the present invention are described in Hiraishi, H. et al. (1999) J. Biochem. (Tokyo) 126, 368-374, Kuba, M. et al. (1992) Eur. J. Biochem. 208, 747-752 and WO 00/52175.

Within the meaning of the present invention the term "protein phosphoamidase" defines a phosphoamidase hydrolyzing phosphoamide (P—N) bonds of phosphorylated basic amino acids like P-His, P-Lys or P-Arg only within peptides or proteins and which is devoid of an activity that hydrolyzes O-phosphorylated proteins or peptides. An example for such a protein phosphoamidase within the meaning of the present invention is the protein histidine-phosphate specific phosphoamidase PHP1 described in WO 00/52175.

Within the meaning of the present invention the term "protein histidine-phosphoamidase" defines a protein phosphoamidase specific for hydrolyzing phosphorylated histidine within peptides or proteins. An example within the meaning of the present invention is PHP1 as described in WO 00/52175.

Within the meaning of the present invention the term phosphatase defines an enzyme hydrolyzing phosphoester (P—O) bonds of phosphorylated amino acids like P-Thr, P-Ser or P-Tyr, or of peptides or proteins comprising these phosphorylated amino acids. These enzymes may have additionally a phosphoamidase activity.

Within the meaning of the present invention the term "protein phosphatase" defines a phosphatase hydrolyzing phosphoester (P—O) bonds of phosphorylated amino acids like P-Thr, P-Ser or P-Tyr only within peptides or proteins. These enzymes may have additionally a phosphoamidase activity. Examples for protein phosphatases within the meaning of the present invention are PP1, PP2A and PP2C (Kim, Y. et al. (1993) *J. Biol. Chem.* 268, 18513-18518).

Within the meaning of the present invention the term "phosphoamidase activity" defines the hydrolyzation of a phosphoamide bond irrespective whether it is hydrolyzed by a phosphoamidase or phosphatase.

Within the meaning of the present invention the term "activity of a phosphoamidase" defines the hydrolyzation of a phosphoamide bond by a phosphoamidase, protein phosphoamidase or protein histidine phosphoamidase which is devoid of an activity that hydrolyzes phosphoester (P—O) bonds of phosphorylated proteins or peptides.

There is some literature on biochemical methods suitable for detection of phosphohistidine dephosphorylation. For example the malachite green method (Ohmori, H. et al. (1993) *J. Biol. Chem.* 268, 7625-7627; Ohmori, H. et al. (1994) *J. Biochem.* 116, 380-385) has been used to identify phosphoamidase activity for 6-phospholysine and 3-phosphohistidine. Released $P_i$ was assayed successive addition of malachite green and citric acid. The absorbance of the phosphate/molybdate complex was measured at 630 nm (Kuba, M. et al. (1992) *Eur. J. Biochem.* 208, 747-752). However this assay may strongly interfere with the acid lability of physiological phosphoamidase substrates. 6-phospholysine, 3-phosphohistidine and the corresponding dephosphorylated amino acids have been identified by thin layer electrophoresis on cellulose and staining with ninhydrin or Rosenberg's reagent.

Using $^{32}P$-labeled histidine-phosphorylated histone H4, the protein phosphatases PP1, PP2A and PP2C have been shown to have a protein phosphoamidase activity for histidine in addition to their Ser-, Thr- or Tyr-phosphatase activity (Kim, Y. et al. (1993) *J. Biol. Chem.* 268, 18513-18518; Matthews, H. R. & MacKintosh, C. (1995) *FEBS Lett.* 364, 51-54; Kim, Y. et al. (1995) *Biochim. Biophys. Acta* 1268 221-228). Phosphoamidase activity for histidine was detected by incubation of [$^{32}P$]histone 4 with phosphatase and subsequent acrylamide-electrophoresis of the reaction mixture and autoradigraphy of the gel. For quantitative analysis $^{32}P_i$ released from [$^{32}P$]histone 4 was removed by ultracentifugation, and the remaining histone-bound phosphate was quantified by liquid scintillation counting.

A further test on the activity of a protein His-phosphoamidase has been described in WO 00/52175 using $^{32}P$-labeled histidine-phosphorylated CheA as substrate. CheA is a recombinant bacterial histidine autokinase (Bilwes, A. M. et al. (1999) *Cell* 96, 131-134). Free phosphate has been identified by thin-layer chromatography via ammonium molybdate or by autoradiography, respectively.

A further possibility to detect inorganic phosphate has been described in WO 95/02825 and Brune et al. 1994 (*Biochemistry* (1994) 33, 8262-8271). This assay is based on the rapid shift in the fluorescence characteristics of MDCC-PBP, which is the *E. coli* phosphate binding protein (PBP) labelled with N-[2-(1)-maleimidyl)ethyl]-7-(diethylamino)coumarin-3-carboxamide (MDCC), a detectable fluorescent label.

However, because the methods mentioned above can not be used in a continuous assay, or are time consuming and/or generate radioactive waste, they are not well applicable in HTS (High Throughput Screening) runs. Therefore there is a need of further protein phosphoamidase and phosphoamidase assays which are easy to perform and applicable in HTS runs.

SUMMARY OF THE INVENTION

The present invention relates to the use of the compounds FDP (fluorescein diphosphate), DDAO (9H-(1,3-dichloro-9,9-dimethyl-acridin-2-one-7-yl)phosphate) DIFMUP (6,8-difluoro-4-methylum-belliferyl phosphate), ELF®39 phosphate (2-(2'-phosphophenyl)-4-(3H)-quinazolinone) and ELF®97 phosphate (2-(5'-chloro-2'-phosphophenyl)-6-chloro-4-(3H)-quinazolinone) (all available from Molecular probes, Inc., Eugene Oreg.) for the detection, characterization and qualitative and/or quantitative determination of the activity of phospho-amidases or protein phosphoamidases independent from the availability of a physiological substrate, which is often unknown for novel enzymes. Such compounds are of interest in relation to characterize the physiological role of phosphoamidases or protein phosphoamidases and to identify their enzyme-substrate specificity unequivocally, and to develop tools to interfere by means of an inhibition or activation of the enzyme.

In a further aspect, the invention relates to methods for the identification of a test substance as an inhibitor or activator of phosphoamidases and/or protein phosphoamidases. Such a method may comprise the steps:

a) establishing a sample comprising the phosphoamidase or protein phosphoamidase and a test substance,
b) administering FDP, DDAO, DiFMUP, ELF®39 phosphate and ELF®97 phosphate to the sample,
c) detecting the signal produced by the substrate, and
d) identifying the test substance as an activator or inhibitor of the phosphoamidase or protein phosphoamidase by comparing the signal produced in the sample comprising the test substance with the signal produced in a control sample comprising no test substance.

Its another embodiment of the invention to provide methods for the detection of phoasphoamidases on native gels, SDS-gels or blots thereof by incubating the gels or blots with ELF®39 phosphate and/or ELF®97 phosphate after electrophoresis and detecting the fluorescence produced by the substrates after reaction with the enzymes for example by a standard tabletop UV-illuminator.

Furthermore the present invention provides methods to identifiy inhibitors or activators specific for a distinct phosphoamidase in a sample comprising other phosphoamidases or phosphatases by incubating the gels or blots after electrophoresis with the substance to be tested and subsequently with ELF®39 phosphate and/or ELF®97 phosphate. The specifity of the inhibitor can be determined by comparing the signals produced in the gel incubated with the test substance with the signals in a control gel without test substance.

Other objects of the present invention are apparent for someone skilled in the art on the basis of the following detailed description.

DETAILED DESCRIPTION OF THE INVENTION

In general, assays for the determination of protein phosphatase activity are frequently based on the determination of released inorganic phosphate from chromogenic or fluorogenic substrates.

Several phosphatases recognize mono- or diphosphate esters of small fluorophore or chromophore compounds as artificial substrates, cleave the phosphate ester bonds and thereby release the fluorophore or chromophore respectively. These substrates have a fluorophor or chromophore with hydroxyl moieties in common that form an ester bond with a phosphate group. They are frequently used in phosphatase assays e.g. for alkaline phosphatase (AP) or PP2A. The phosphatase activity is followed by the increased fluorescence or absorption response of the reaction product. Due to different chemical properties like the pKa of the phosphate ester, the substrates DiFMUP (6,8-difluoro-4-methylum-belliferyl phosphate) (Gee, K. R. et al. (1999) *Anal. Biochem.* 273, 41-48), MUP (4-methylumbelliferyl phosphate) (Anthony, F. A. et al. (1986) *Anal. Biochem.* 155, 103-107; Rietz, B. & Guilbault, G. G. (1975) *Clin. Chem.* 21, 1791-1794), DDAO (9H-(1,3-dichloro-9,9-dimethyl-acridin-2-one-7-yl)phosphate) (Leira, F. et al. (2000) *Toxicon* 38, 1833-1844), FDP (fluorescein diphosphate) (Huang, Z. et al. (1999) *J. Biomol. Screen.* 4, 327-334), pNPP (para-nitrophenol phosphate) and DCAP (Osawa, S. et al. (1995) *Clin. Chem.* 41, 200-203) are compatible with a broad range of phosphatases.

The protein histidine phosphoamidase PHP1 neither hydrolyzes phosphoester (P—O) bonds of phosphorylated proteins or peptides (see FIGS. 2-6) nor it accepts the phosphate ester pNPP, a commonly used substrate of phosphatases like PP2A and acid phosphatase. Also MUP, a substrate of AP, PP1, PP2A and acid phosphatase is not accepted as substrate by PHP1 (see FIG. 1). It was therefore surprising that PHP1 accepts DiFMUP, a fluorinated derivative of MUP, FDP, DDAO, ELF®39 phosphate and ELF®97 phosphate (see FIGS. 1 and 7 to 11) as substrates although these compounds are phosphate esters as well as pNPP and MUP.

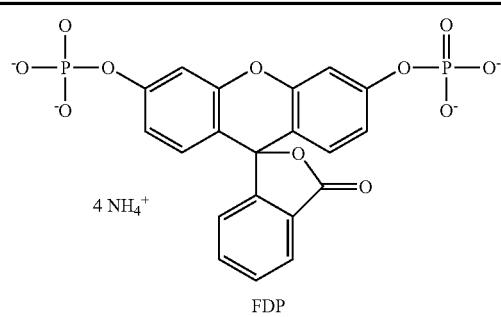

FDP

-continued

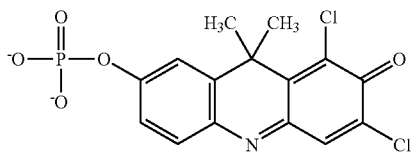

2 NH$_4^+$

DDAO phosphate

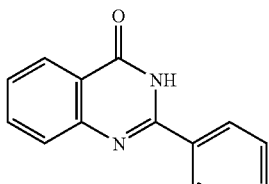

2 Na$^+$

ELF39 phosphate

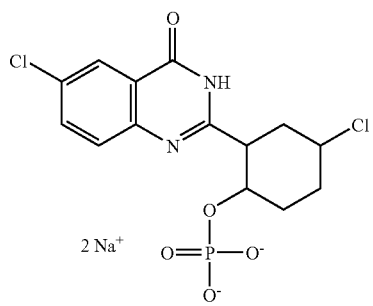

2 Na$^+$

ELF97 phosphate

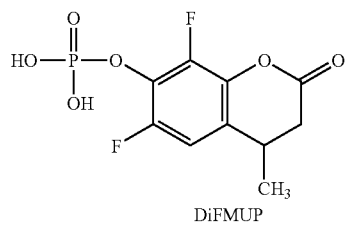

DiFMUP

MUP

Figure 2:
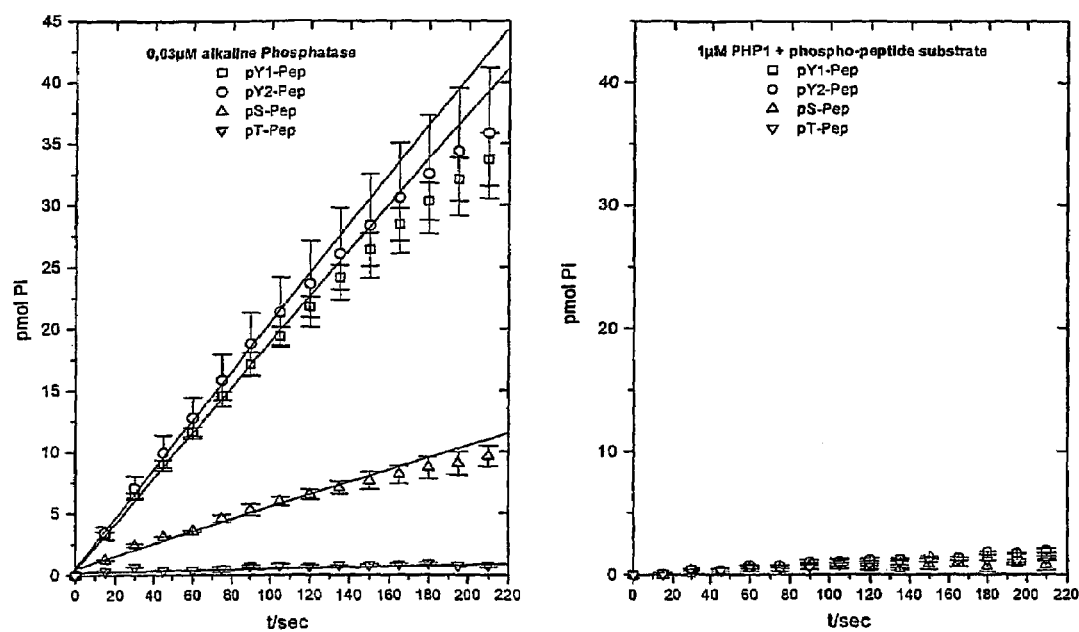
FIG. 2: Time resolved measurement of phosphate released from phospho-peptides by alkaline phosphatase (AP) (left diagram) and PHP1 (right diagram). The fluorescence signal is converted into phosphate concentration using a normalizing factor derived from standard curve titration of inorganic phosphate with fluorescent phosphate binding protein.

For example, FIG. 2 (left panel) shows the reactivity of AP with the commonly used and commercially available substrates for protein phosphatases, pY1 (Sequence: RRLIEDAEpYAARG), pY2 (Sequence: TSTEPQpYQP-GENL), pS (Sequence: RRApSVA) and pT (Sequence: KRpTIRR). For the detection of phosphate released from the peptides the MDCC-PBP-assay has been used as described in the examples. The phospho-tyrosine peptides pY1 and pY2 are dephosphorylated by AP with a velocity (pmolPi/min) of 11 for pY1 and about 12 for pY2 and a specific activity (nmol/min*mg) of about 33 for pY1 and about 36 for pY2. To a smaller extend the phospho-serine peptide pS is dephosphorylated with a velocity of 3 and a specific activity of 9. The phospho-threonine peptide pT is not dephosphorylated by AP.

Figure 3:
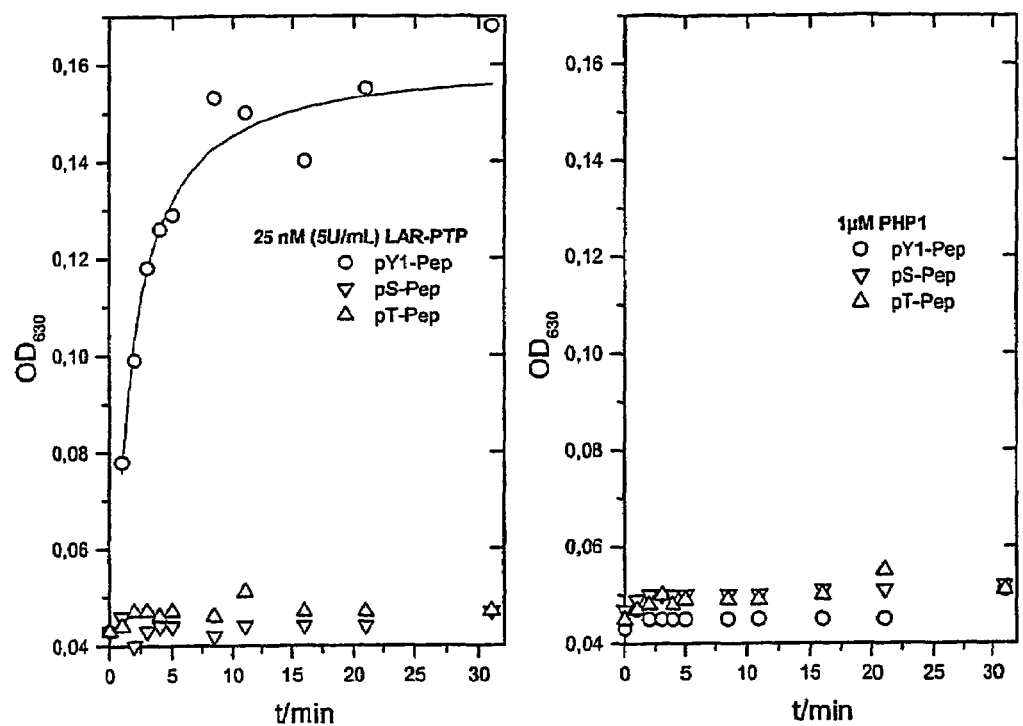
FIG. 3: Detection of phosphatase activity using the malachite green assay for the reaction of LAR-PTP (left diagram) and of PHP1 (right diagram) with phospho-peptides.

As shown in FIG. 3 (left panel), the protein tyrosine-phosphatase LAR (LAR-PTP) dephosphorylates the phospho-tyrosine peptide but neither the phospho-serine peptide nor the phospho-threonine peptide. In these experiments the malachite green assay as described in the examples has been used for the detection of phosphate released from the peptides. In strong contrast, using PHP1 as enzyme (FIGS. 2 and 3, right panels) the dephosphorylating activity does not exceed the blank value although the enzyme concentration was 30-fold higher than that of AP and 40-fold higher than that of LAR-PTP.

These results were verified by the use of mass spectrometry (see FIGS. 4-6), which is a powerful tool to the identity of biopolymers by their individual masses. The phospho-peptide substrates have masses of 700-1500 Da and will loose 80 Da upon cleavage of the phosphate group. This mass difference is easily detected with high mass accuracy in a MALDI-TOF spectrometer. Moreover it is a well accepted fact, that dephosphorylated peptides are more easily detected in mass spectrometers than their phosphorylated counterparts (Sickmann, A. & Meyer, H E (2001) *Proteomics* 1, 200-206). Hence even a small fraction of converted peptides will be detectable if the substrate is accepted by the respective phosphatase. Another advantage of this method is that the nature of the substrate entity is directly monitored. Even MALDI-induced dephosphorylation can be easily distinguished from enzymatic dephosphorylation in case of phospho-serine and -threonine residues as the first will produce mass differences of 98 Da instead of $\Delta m=80$ Da in the latter case.

Figure 4:
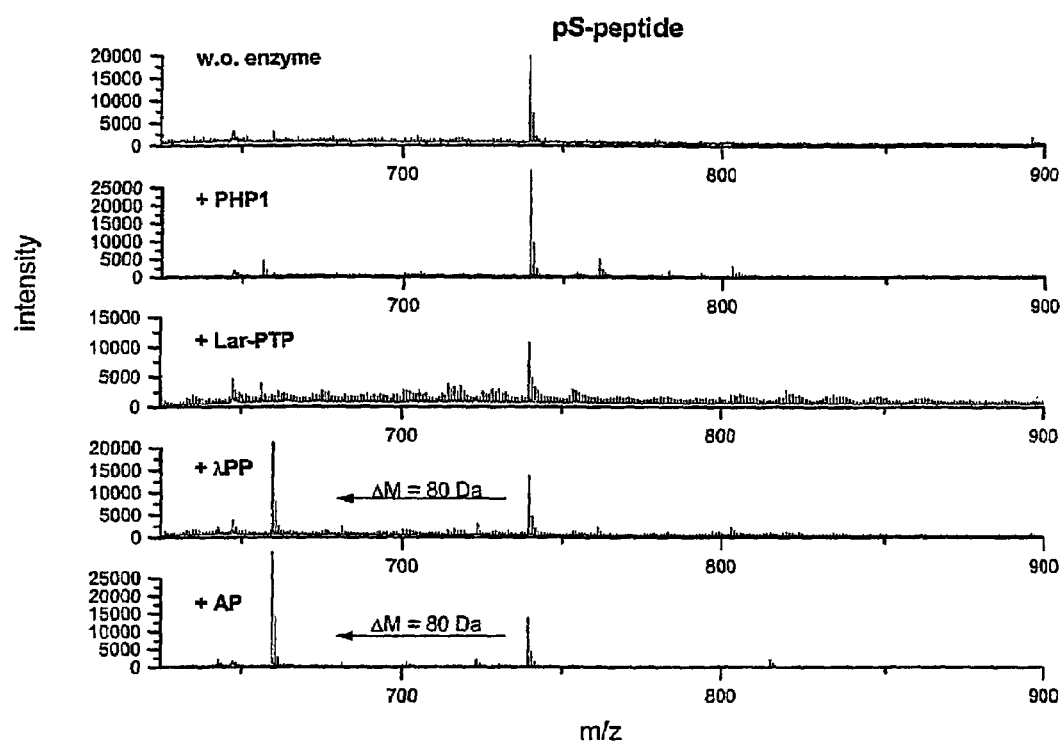
FIG. 4: Mass spectrometric analysis of the reaction product of incubating phosphopeptides with individual phosphatases/phosphoamidases. The loss of 80 Da in mass indicates the enzymatic cleavage of phosphate from the pS-peptide by λPP and AP.

The mass spectrometric analysis show that the pS-peptide was recognized as phosphatase substrate by λPP and AP but neither by Lar-PTP nor by PHP1 (FIG. 4). After incubation with either λPP or AP a major fraction becomes dephosphorylated within the reaction time and a species with a mass reduced by 80 Da corresponding to the dephosphorylated peptide can be detected. The pS-peptide incubated with Lar-PTP or either PHP1 does not cleave at all.

Figure 5:
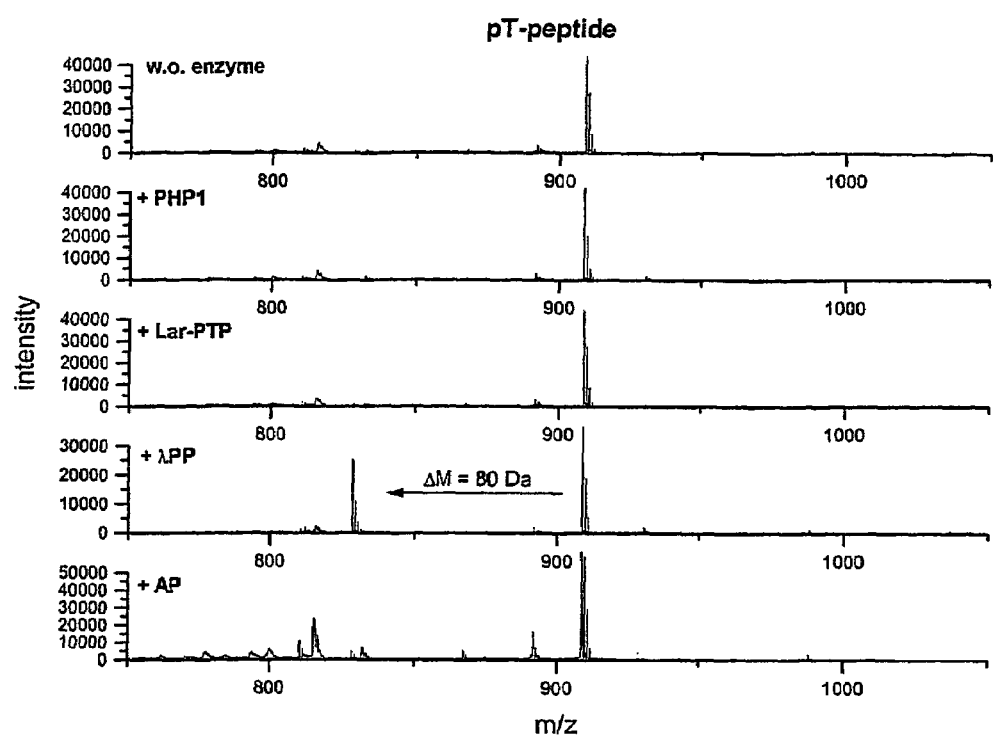
FIG. 5: Mass spectrometric analysis of the reaction product of incubating phosphopeptides with individual phosphatases/phosphoamidases. The loss of 80 Da in mass indicates the enzymatic cleavage of phosphate from the pT-peptide by λPP and AP.

The mass spectrometric analysis shows that the pT-peptide was recognised as phosphatase substrate solely by λPP but neither by Lar-PTP nor by PHP1 or AP (FIG. 5). After incubation with λPP a substantial fraction becomes dephosphorylated within the reaction time and a species with a mass reduced by 80 Da corresponding to the dephosphorylated peptide can be detected. The pT-peptide incubated with Lar-PTP, AP or by PHP1 does not change at all.

In contrast to phospho-serine and -threonine residues the phospho-tyrosine peptide exhibits a substantial fraction of dephosphorylated species even in the control sample. The origin of this species remains uncertain, as phospho-tyrosine may eliminate phosphoric acid under MALDI-conditions that would equal a loss of $\Delta m=80$ Da. This is essentially the same mass difference observed after enzymatic cleavage.

Figure 6:
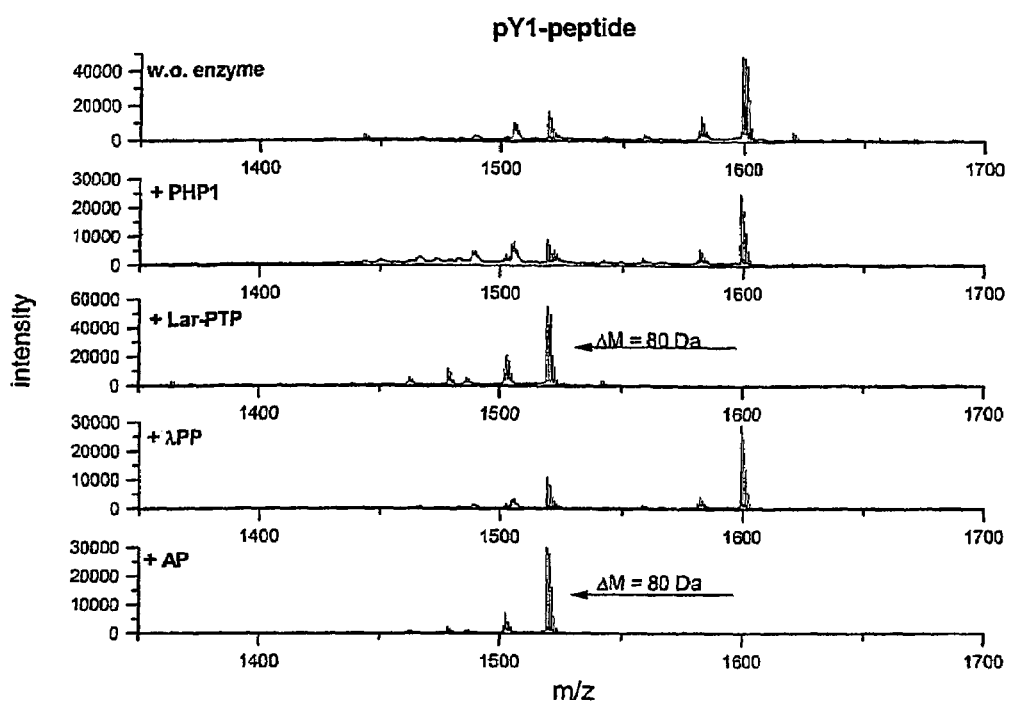
FIG. 6: Mass spectrometric analysis of the reaction product of incubating phosphopeptides with individual phosphatases/phosphoamidases. The loss of 80 Da in mass indicates the enzymatic cleavage of phosphate from the pY1-peptide by Lar-PTP and AP.

The mass spectrometric analysis shows that the pY-peptide was recognised as phosphatase substrate by Lar-PTP and AP but neither by λPP nor by PHP1 (FIG. 6). After incubation with either Lar-PTP or AP the peptide becomes completely dephosphorylated within the reaction time and a species with a mass reduced by 80 Da corresponding to the dephosphorylated peptide can be detected. The pT-peptide incubated with λPP or PHP1 does not change at all as compared to the control sample.

In summary, in none of the reaction mixtures a phosphopeptide was accepted as a substrate for PHP1 but indeed for the other phosphatases tested with the expected substrate specificities.

As a result of the finding that the compounds FDP, DDAO DIFMUP, ELF®39 phosphate and ELF®97 phosphate are substrates for phosphoamidases and protein phosphoamidases like PHP1, the present invention provides easily executable continuous enzymatic assays for the determination of phosphoamidases and protein phosphoamidases.

Figure 1:
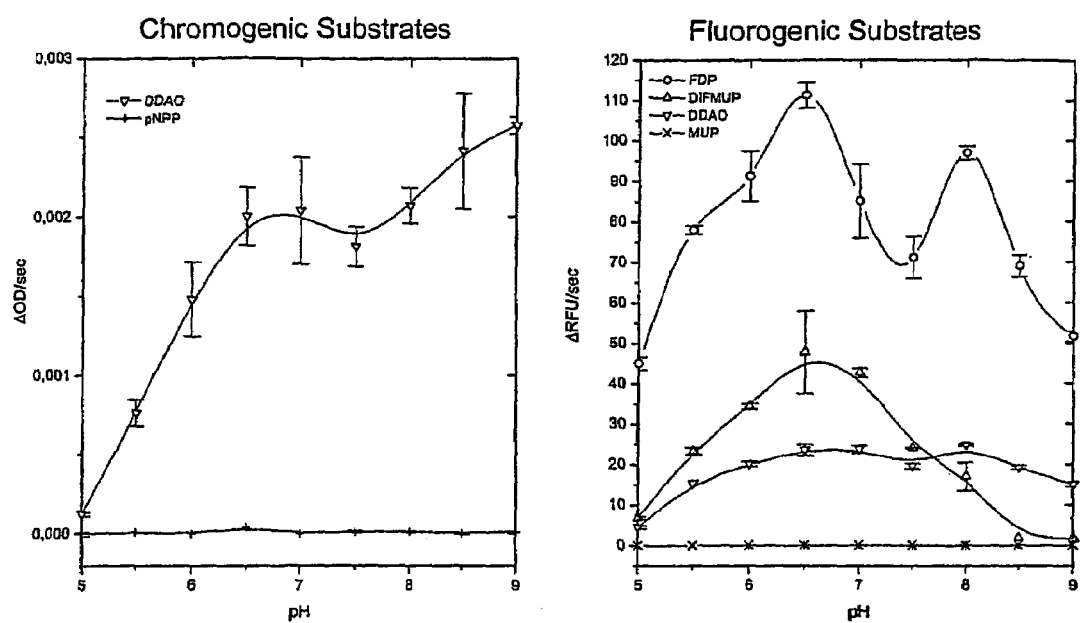
FIG. 1: pH-dependence of initial reaction rates of the conversion of fluorogenic and chromogenic substrates by PHP1.

Because it is well known that the use of phospho fluorophores like DIFMUP, MUP, DDAO or FDP as phosphatase substrates have certain limitations due to the compatibility of the substrate pKa-values with the pH-optima of the respective phosphatase, the pH-dependence of the PHP1 reactivity towards the aforementioned fluorogenic substrates is to be determined. As shown in FIG. 1 the pH is varied from pH=5-9 in steps of 0.5 pH-units. In order to avoid undesired fluorescence flattening effects due to high absorption by the accumulating reaction product the initial reaction velocity is used as relative measure for the pH-dependence of PHP1-reactivity towards the selected substrate. This approach gives reasonable results for MUP, DIFMUP and FDP but not for DDAO even at 25 µM dilution. The latter therefor may provide high sensitivity for trace detection of phosphatase activity, but may not be optimal for the use as a substrate above low µM-concentrations e.g. for studies of enzyme kinetics.

From this experiment a clear substrate selectivity of PHP1-towards the phosphate esters DiFMUP, DDAO, FDP as substrate becomes evident. As mentioned above, the most widely used artificial phosphatase substrate with broad applicability pNPP as well as the typical alkaline phosphatase substrate MUP are not recognised and processed by PHP1 at any pH. The titration curves of the other substrates show very distinct shapes that may reflect both the pH-dependence of the enzymatic reaction and the chemical properties, like the protonation grade of the fluorophores. All three, DiFMUP, FDP and DDAO show increasing turnover rates measured at their standard emission wavelengths when the pH is shifted from acidic to neutral with a maximum at pH=6.5-7. The optimum pH for PHP1 is known to be at about a pH of 6 but an overlaying effect due to protonation of the fluorophore and shift in spectral properties is obvious from a colour change of all samples in acidic media. While DIFMUP reveals a decrease in turnover rate in more alkaline media DDAO turnover stays relatively constant and the curve for FDP exhibits a second distinct maximum. The cause for the latter observations may originate from two populations of singly and doubly dephosphorylated FDP with individual spectral properties or substrate recognition by PHP1.

Figure 7:
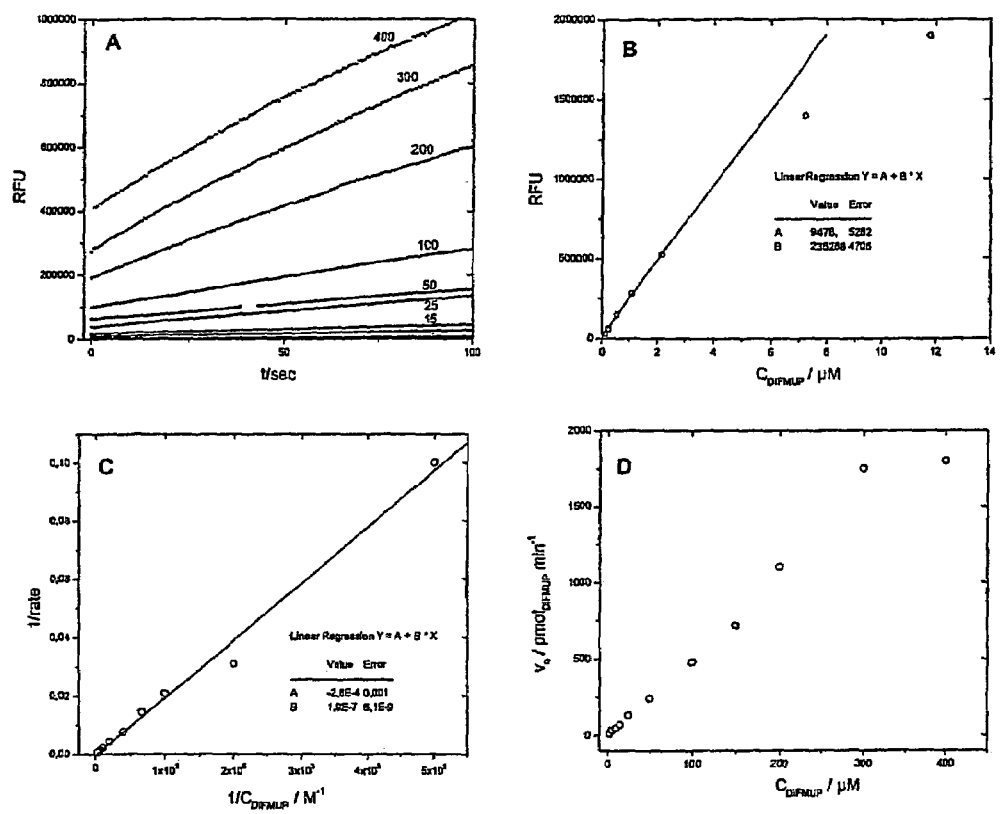
FIG. 7: Kinetic analysis of the conversion of DiFMUP by PHP1:
A) Increase in fluorescence due to the dephosphorylation of DiFMUP at various substrate concentrations (in pM). The increase in initial fluorescence signal is due to the background fluorescence of unreacted substrate.
B) Correlation of relative fluorescence with the concentration of fully converted substrate for quantification purpose.
C) Lineweaver-Burk plot of inversed initial rates versus inversed DiFMUP-concentration with linear fit.
D) Michaelis-Menten plot of initial reaction velocities versus substrate concentration. The linear correlation does not allow for non-linear curve fit deriving the Michaelis-Menten parameter.
Figure 8:
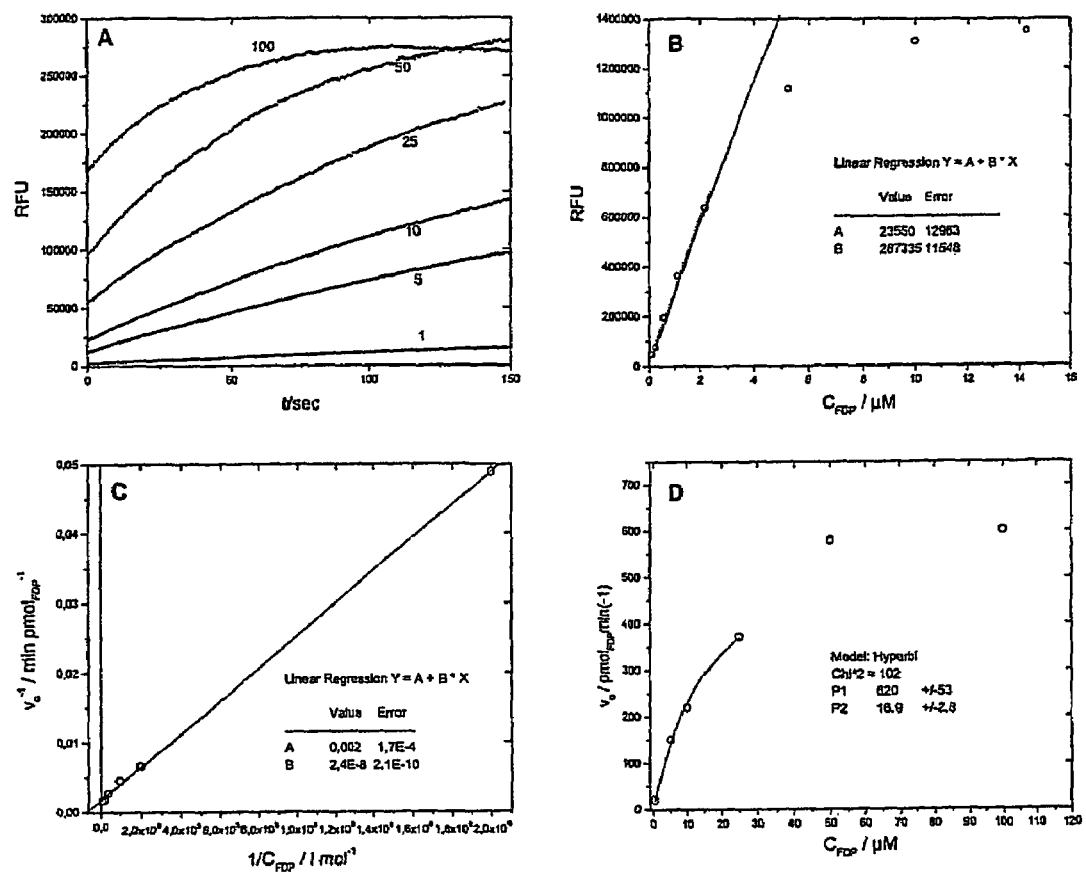
FIG. 8: Kinetic analysis of the conversion of FDP by PHP1:
A) Increase in fluorescence due to the dephosphorylation of FDP at various substrate concentrations (in μM). The increase in initial fluorescence signal is due to the background fluorescence of unreacted substrate.
B) Correlation of relative fluorescence with the concentration of fully converted substrate for quantification purpose.
C) Lineweaver-Burk plot of inverse initial rates versus inverse FDP-concentration with linear fit.
D) Michaelis-Menten Plot of initial reaction velocities versus substrate concentration. The hyperbola correlation does allow for non-linear: curve fit deriving the Michaelis-Menten parameter.

In further experiments the $K_M$-values for the reaction of PHP1 with DiFMUP and FDP have been determined (see FIGS. 7 and 8). The $K_M$-values for DiFMUP and FDP can be approximated by recording the initial reaction velocity in dependence of the substrate concentration, as observed by the increase in relative fluorescence at the respective fluorescence emission maxima upon addition of PHP1. The reaction velocity of the DiFMUP and FDP conversion by PHP1 is clearly dependent from the substrate concentration. From the titration experiments with fully converted substrate it becomes obvious, that signal saturation occurs within the low µM range, particularly for the fluoresceine derivative FDP. This effect limits the range of substrate variation. For FDP concentrations >20 µM the signal quenching disturbs reaction rate measurements detrimentally. However data analysis using non-liner curve fit with a hyperbola function allows deducing a Michaelis constant of $K_M \approx 20$ µM with a high uncertainty. Measurements for DiFMUP are limited to concentrations below 500 µM. Despite this higher range for substrate variation no saturation in initial reaction rate could be observed as the correlation between rates and substrate concentration remained linear. From the Lineweaver-Burk plot the $K_M$-value might be estimated to exceed 1 mM. From literature $K_M$ values of 20 µM are known e.g. for the enzymatic reaction of T-cell tyrosine phosphatase on DIFMUP (Kerby, M. et al. (2001) *Electrophoresis* 22, 3916-3923). The higher value for the reaction of PHP1 on DiFMUP might reflect the less accurate substrate acceptance of PHP1 for phosphate ester substrates. In this regard FDP is not comparable to DiFMUP as it bears two phosphate groups and this will certainly improve enzyme substrate interaction.

Figure 9:
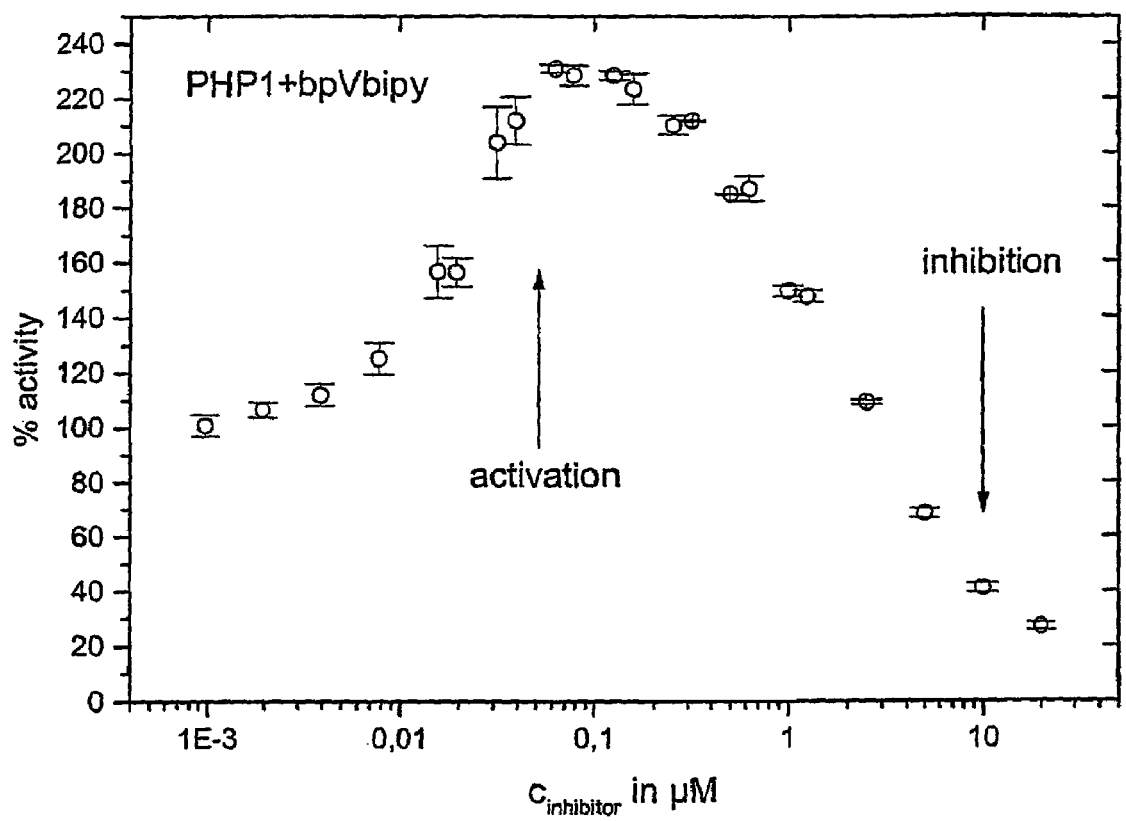
FIG. 9 Plot of inhibitor concentration vs. DifMUP-readout after 5 min reaction time at 0.1 μM PHP1 concentration.

In order to test whether the phosphoamidase and protein phosphoamidase substrates of the present invention are suitable for the for identification of inhibitors or activators of these proteins, the activity of PHP1 was determined with the substrate DiFMUP in presence of bisperoxo-(bipyridine)-oxovanadate [(bp)V(bipy)], a well characterized inhibitor of protein phosphotyrosine phosphatase(FIG. 9). The inhibitor concentration varied from 0.01 to 30 µM, the enzyme concentration was kept at 0.1 µM and substrate concentration at 50 µM. After incubation for 15 min at room temperature the fluorescence was detected at 450 nm on excitation at 360 nm. The assay yielded a reproducible and clearly dose-dependent inhibition of PHP1 activity for (bp)V(bipy). Surprisingly the (bp)V(bipy) compound activated the PHP1 activity at equimolar concentrations by a factor of two and showed an inhibitory effect only above 10 µM.

It becomes clear from these experiments that the phosphoamidase and protein phosphoamidase substrates FDP, DDAO DiFMUP, ELF®39 phosphate and ELF®97 phosphate are suitable for the identification of inhibitors or activators of these enzymes. These substrates allow the implementation of easily executable, time saving and no radioactive waste generating enzymatic assays, also applicable in HTS runs.

The compounds ELF®39 phosphate and ELF®97 phosphate are fluorogenic substrates for alkaline phosphatases designed for applications in immunoblots and histological stains of enzyme activity. These substrates have the properties to be converted into an insoluble strongly fluorescent precipitate upon phosphate cleavage at the specific location of phosphatase activity. Usually AP is detected by the substrate conversion due to the high specific activity compared to other phosphatases and a wide substrate specificity of this enzyme.

Figure 10:
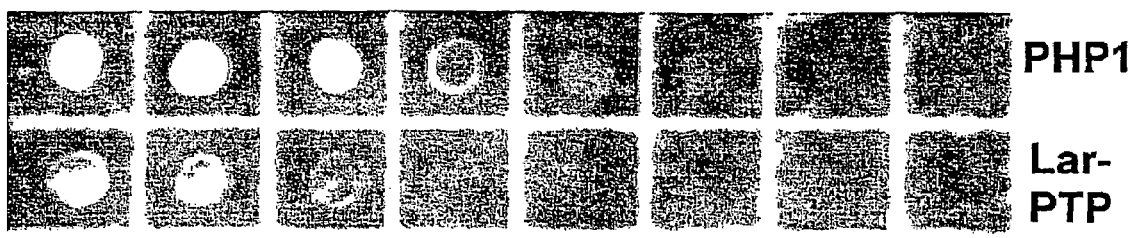
FIG. 10: Dot-blot with serial dilution of PHP1 (5 μg, 2.5 μg, 1.3 μg, 0.6 μg, 0.3 μg, 0.15 μg, 0.08 μg, 0.04 μg) and Lar-PTP (1 μg, 0.5 μg, 0.25 μg, 0.13 μg, 0.06 μg, 0.03 μg, 0.015 μg, 0.08 μg).
Figure 11:
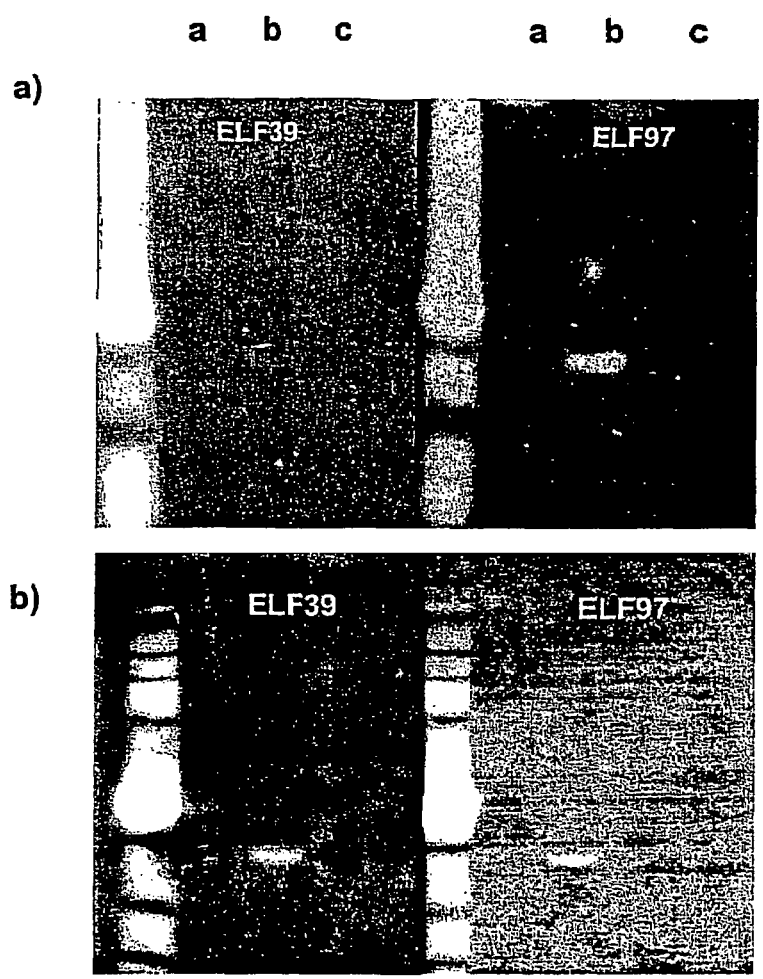
FIG. 11: a) Image of SDS-PAGEs after separation of I) AP, II) PHP1 and III) Lar-PTP (each 5 μg) and subsequent renaturation and soaking with fluorogenic substrates (ELF®39 phosphate and ELF®97 phosphate). The first lane was loaded with pre-stained protein marker, that exhibits auto-fluorescence.
b) Image of Western blots corresponding to the SDS-PAGEs shown in FIG. 8A) after separation of a) AP, b) PHP1 and c) Lar-PTP (each 5 μg) and subsequent renaturation and soaking with fluorogenic substrates (ELF®39 phosphate and ELF®97 phosphate). The first lane was loaded with prestained protein marker, that exhibits auto-fluorescence.

Unexpectedly PHP1 recognizes both fluorogenic substrates ELF®39 phosphate and ELF®97 phosphate as substrates. FIG. 10 shows a dot blot of a dilution series of PHP1 and LAR-PTP after subsequent incubation with the ELF®97 phosphate substrate solution.

As demonstrated in FIG. 10, PHP1 shows a distinct signal at enzyme quantities under 100 ng even though if a relatively insensitive detection set-up is used. The production of the fluorescent precipitate at the side of phosphoamidase activity in principle allows any kind of spatial resolution but does not give any clue to the nature of the phosphoamidase. The combination of the separation of proteins by SDS-PAGE, native gel electrophoresis, 2D-electrophoresis or isoelectric focussing with the enzyme can circumvent this problem. Commonly enzyme activity is detected after electrophoresis by extracting the enzyme from the polyacryamide matrix or by converting substrates that have been co-polymerised in the polyacrylamide matrix or co-migrated into the gel with the enzyme sample. Soaking the gel with small artificial substrates provides an alternative that is already used but with the frequent disadvantage that such substrate retain soluble and diffuse back from gel to bulk solution once they are converted. ELF®39 phosphate and ELF®97 phosphate represent unique substrates which change not only spectral properties but also their solubility and therefore remain within the gel where the phosphatase or phosphoamidase is located. An important issue is that the phosphoamidases have to be renatured at least for the part of the catalytic domain after the denaturing SDS-PAGE or 2D-electrophoresis has been performed.

In the experiments presented in FIGS. 11a) and 11b) samples of a) AP, b) PHP1 and c) Lar-PTP (each 5 µg) have been separated on 10% NOVEX® NuPAGE®. Both, the SDS-PAGE and the western blots demonstrate that PHP1 was renatured after separation and was able to convert the fluorogenic substrates ELF®39 phosphate and ELF®97 phosphate into the desired fluorescent precipitates. These precipitates accumulate at the location of the PHP1 protein band in the SDS Page, with the expected apparent molecular weight of 14 kDa (estimated from the protein marker and coomassie counter staining).

With these substrates it is also possible to determine whether a certain inhibitor or activator acts specific on only one phosphoamidase or phosphatase in a sample comprising other phosphoamidases or phosphatases or whether the inhibitor or activator inhibits or activates several phosphoamidases or phosphatases. For that, a sample comprising several phosphoamidases and/or phosphatases is separated for example by native electrophoresis. Subsequently the gel is equilibrated in a first step with the inhibitor or activator and in the second step with ELF®39 phosphate and/or ELF®97 phosphate. The specifity of the inhibitor or activator can be determined by comparing the signal produced in the gel incubated with the inhibitor or activator with the signals in a control gel without test substance. For example, if the sample separated by gel electrophoresis contains five different phosphatases or phosphoamidases which react with ELF®39 phosphate and/or ELF®97 phosphate, the gel will show five spots resulting from the dephosphorylation of the substrate. If a second gel is incubated with an inhibitor specific for only one of the phosphatases or phosphoamidases the subsequent incubation with ELF®39 phosphate and/or ELF®97 phosphate will result in only four spots. By comparing the gel containing no inhibitor with the gel incubated with the inhibitor the specificity of the inhibitor can be evaluated. If instead of a native gel a SDS- or IEF-gel is used, it has to be assured that the proteins of interest have been renatured.

EXAMPLES

Analysis of Phosphatase/Phosphoamidase Activity

In order to evaluate the substrate specificity of PHP1 towards other phosphorylated peptide sequences synthetic phospho-peptides have been selected as artificial substrates. These commercially available peptides (Upstate Inc., Waltham, Mass.) are commonly used substrates for protein phosphatases that dephosphorylate phospho-serine phospho-threonine or phospho-tyrosine with the respective sensitivities:

| Name | Kind of phosphopeptide | Sequence | Source |
|------|------------------------|----------|--------|
| pY1 | Tyrosine phosphopeptide | RRLIEDAEpYAARG | Upstate Inc., Waltham, MA |
| pY2 | Tyrosine phosphopeptide | TSTEPQpYQPGENL | Upstate Inc., Waltham, MA |
| PS | Serine phosphopeptide | RRApSVA | Upstate Inc., Waltham, MA |
| PT | Threonine phosphopeptide | KRpTIRR | Upstate Inc., Waltham, MA |

The phosphatases used for comparative studies of substrate recognition are LAR-PTP (tyrosine phosphatase LAR, recombinant), λ-PP (protein phosphatase lambda, recombinant) and AP (alkaline phosphatase, bovine intestine).

The enzyme concentrations are individually adjusted for every experimental set up in the fashion that enzymatic reactions can be monitored in a linear regime on the second to minute time scale.

a) MDCC-PBP-Assay

In a first set of experiments the phosphatase reaction of PHP1 is compared with that of alkaline phosphatase using the above mentioned phosphopeptides as substrates. In order to follow the reaction continuously the phosphate entity that was cleaved of by the phosphatase is detected using the coumaryl labelled phosphate binding protein MDCC-PBP (WO95/02825; Brune et al. (1994) *Biochemistry* 33, 8262-8271) which is available from the Medical Research Council, London, UK. In a first step the basal level of free phosphate in solutions of 40 µM phospho-peptide (in assay buffer: 25 mM Hepes pH 7.0, 1 mM $MgCl_2$, 20 mM NaCl, 0.01 mg/ml BSA) has to be determined by titration versus a solution of 4 µM phosphate binding protein. Non of the peptide solutions exceeded 0.5 mol % of free phosphate/peptide. The phosphatase/phosphoamidase reaction was performed by mixing 50 µl of peptide solution (20 µM final concentration) with 50 µl 6 µM MDCC-PBP dilution in assay buffer in white microplates at room temperature and finally by adding 50 µl of the phosphatase or phosphoamidase solution. The final concentration of the enzymes in the test solution are 0.035 µM for AP and 1 µM for PHP1. The increase in fluorescence (Ex 425 nm; Em 465 nm) is measured time resolved using a standard microplate reader.

b) Malachite Green Assay:

The enzymatic reaction of Lar-protein tyrosine phosphatase towards the phosphopeptides is compared to that of PHP1 using the classical malachite phosphate assay. Inorganic phosphate cleaved from the peptide substrate is detected as a green co-complex with molybdate and malachite dye. The phosphatase reaction is performed by mixing 950 µl of peptide solution (50 µM final concentration) with 50 µl of the phosphatase/phosphoamidase solution, both stock solutions were prepared in standard assay-buffer (25 mM Hepes pH 7.0, 1 mM $MgCl_2$, 20 mM NaCl, 0.01 mg/ml BSA;). The final concentration of the enzymes in the test solution are 0.025 µM for Lar-PTP and 1 µM for PHP1. After discrete time intervals a 50 µl sample of each reaction mixture was mixed with the molybdate/malachite detection solution (BIOMOL) and incubated at room temperature. The release of phosphate was identified by the increase of absorption at 630 nm.

pH-Dependence of PHP1 Assays

The reaction mixture was prepared by diluting the substrate from the 10 mM stock solution in DMSO into the aqueous reaction buffer consisting of 25 mM buffering substance, 20 mM NaCl, 1 mM $MgCl_2$, 0.1 mg/ml BSA to yield a final concentration of 100 µM for MUP and DiFMUP or 25 µM for DDAO and FDP respectively. As buffering substance MES/NaOH was used for pH-values of 5.0, 5.5, 6.0, 6.5 whereas Tris/HCl was used for pH-values of 7.0, 7.5, 8.0, 8.5, 9.0. To start the reaction PHP1 was added from a pre dilution in the respective reaction buffer to yield a final concentration of 0.1 µM. The reaction was monitored by recording the increase in relative fluorescence at the respective fluorescence emission maxima (Fluoromax Gemini XL microplate reader).

Kinetic Analysis of the Conversion of FDP and DiFMUP by PHP1

The reaction mixture is prepared by diluting the substrate from a 10 mM stock solution in DMSO into the standard aqueous reaction buffer (25 mM HEPES pH=7.0, 20 mM NaCl, 1 mM $MgCl_2$, 0.01 mg/ml BSA) to yield a final concentration ranging from 1-400 µM. To start the reaction PHP1 was added from a stock solution to a final concentration of 0.1 in µM. The reaction was monitored by recording the increase in relative fluorescence at the respective fluorescence emission maxima in an SLM fluorescence spectrometer. To allow for quantification the fluorescence signal was normalised using a standard curve recorded for a serial dilution of fully dephosphorylated DiFMUP and FDP respectively. All recordings were carried out at the same PM-voltage and integration time with correction for the relative signal gain.

Mass-Spectrometric Analysis of Enzyme Activity Towards Synthetic Phosphorylated Peptides The experimental setup is as follows: The phosphopeptide substrate is diluted from stock-solutions to concentrations of 50 µM and mixed with the individual phosphatase to give final enzyme concentrations of 1 µM PHP1, 0.05 µM Lar-PTP, 0.05 µM λPP and 0.05 µM AP.

The mixtures is incubated for 2 h at room temperature and finally spotted in volumes of 0.5 µl onto a MALDI-target. Briefly thereafter the matrix solution of alpha-hydroxycinnaminic acid was added and the droplets were left to dry. Mass spectrometry was performed on a MALDI-TOF spectrometer in reflective mode with delayed extraction.

Screening Assays for Inhibitors or Activators of Protein Phosphoamidases and Phosphoamidases.

The reaction mixtures for inhibitor screening were prepared by serial 2 fold dilution of the inhibitor bpV(bipy) (Alexis Biochemicals San Diego) starting at 60 µM into 50 µl of the assay buffer consisting of 25 mM Hepes pH=7, 20 mM NaCl, 1 mM $MgCl_2$, 0.01 mg/ml BSA. In a next step 50 µl of a solution of 0.3 µM PHP1 in assay buffer was added to each well and incubated for 5 min at room temperature. In order to initiate the reaction a pre dilution of 50 µM DiFMUP-substrate in assay-buffer was rapidly added to all wells. The reaction was monitored by recording the increase in relative fluorescence at the respective fluorescence emission maxima (Fluoromax Gemini XL microplate reader). The relative activity was calculated using the RFU derived from a control reaction without inhibitor.

Detection of of Protein Phosphoamidases and Phosphoamidases in Blots and Gels

To show the utility of ELF®39 phosphate and ELF®97 phosphate for the detection of protein phosphoamidases and phosphoamidases PHP1 and LAR-PTP—are diluted in series by factor 2 with assay buffer (25 mM HEPES pH 7.0, 20 mM NaCl, 1 mM $MgCl_2$, 0.1 mg/ml BSA) and 10 µl of each dilution is spotted on a nitrocellulose membrane. After a short wash (~5 min) in assay buffer the membrane was covered with a solution of the respective substrate (1:20 dilution of supplier stock-solution) in assay buffer and incubated for at least one hour or until a stable signal has developed. Fluorescence is detected on a standard tabletop UV-illuminator (excitation wave length commonly 254 nm or 300-370 nm) or for higher signal selectivity by fluorescence imaging systems equipped with exciting light sources and narrow pass optical filters that allow optimal matching of the ELF®39 and ELF®97 spectral properties.

For the detection of protein phosphoamidase in SDS-Gels AP, PHP1 and Lar-PTP (each 5 µg) have been separated on 10% NuPAGE® BisTris/MES-gel system (Invitrogen®). Sample preparation was by adding reducing NUPAGE® SDS-sample buffer (Invitrogen®) to the enzyme solutions and immediate loading on the gel essentially without previous heating. After separation the gel was either used directly for detection or blotted onto nitrocellulose membrane using NuPAGE® transfer-buffer (Invitrogen®) essentially without methanol. The gels and blots were than washed three times in Tris Buffered Saline, 1 mM $MgCl_2$ by gentle shaking for 30 min at room temperature and subsequently incubated with a solution of the respective substrate (1:20 dilution of supplier stock-solution) in assay buffer (25 mM HEPES pH 7.0, 20 mM NaCl, 1 mM $MgCl_2$, 0.1 mg/ml BSA). After incubation for at least one hour the fluorescence signal was detected as described above.

We claimed:

1. A method for the detection, characterization and qualitative and/or quantitative determination of the activity of a phosphoamidase PHP1 enzyme, comprising hydrolyzing a phospho-ester bond (P—O) of at least one of the substrates which is FDP (fluorescein diphosphate), DDAO (9H-(1,3-dichloro-9,9-dimethyl-acridin-2-one-7-yl)phosphate), DiFMUP (6,8-difluoro-4-methylum-belliferyl phosphate), ELF®39 phosphate (2-(2'-phosphophenyl)-4-(3H)-quinazolinone) or ELF®97 phosphate (2-(5'-chloro-2'-phosphophenyl)-6-chloro-4-(3H)-quinazolinone) and correlating the resultant hydrolysis level with the phosphoamidase activity of said enzyme.

2. A method of claim 1, wherein said method is conducted in liquid phase, semi-solid phase, or solid phase.

3. A method of claim 2 wherein said liquid phase is buffer-based, said semi-solid phase is gel-based, and said solid phase is blot-based.

4. A method for the identification of an inhibitor or activator of protein phosphoamidase PHP1 enzyme comprising:
   a) establishing a sample comprising or protein phosphoamidase PHP1 enzyme and a test substance,
   b) administering a substrate which is FDP, DDAO, DiFMUP, ELF®39 phosphate or ELF®97 phosphate to the sample,
   c) detecting the signal produced by the hydrolysis of the phospho-ester bond (P—O) of the substrate, and
   d) identifying the test substance as an activator or inhibitor of the PHP1 protein phosphoamidase by comparing the signal produced in the sample comprising the test substance with the signal produced in a control sample comprising no test substance.

5. A method of claim 4, wherein said method is conducted in liquid phase, semi-solid phase, or solid phase.

6. A method of claim 5 wherein said liquid phase is buffer-based, said semi-solid phase is gel-based, and said solid phase is blot-based.

7. A method for the identification of an inhibitor or activator of a protein histidine phosphoamidase 1 (PHP1) comprising:
   a) establishing a sample comprising said PHP1 and a test substance,
   b) administering a substrate selected from the group consisting of FDP, DDAO, DiFMUP, ELF®39 phosphate and ELF®97 phosphate to the sample,
   c) detecting the signal produced by the hydrolysis of the phospho-ester bond (P—O) of the substrate, and
   d) identifying the test substance as an activator or inhibitor of said PHP1 by comparing the signal produced in the sample comprising the test substance with the signal produced in a control sample comprising no test substance.

* * * * *